United States Patent [19]

McGee

[11] 4,369,782

[45] Jan. 25, 1983

[54] EYEWASHING APPARATUS

[76] Inventor: Terrill McGee, 525 South Ardmore, #208, Los Angeles, Calif. 90020

[21] Appl. No.: 263,831

[22] Filed: May 15, 1981

[51] Int. Cl.³ .............................................. A61M 7/00
[52] U.S. Cl. ....................................... 128/249; 2/410
[58] Field of Search ........... 128/248, 249, 380, 200.28, 128/76 R, 65–67, 400, 402; 2/410, 422

[56] References Cited

U.S. PATENT DOCUMENTS

| | | | |
|---|---|---|---|
| 1,437,435 | 12/1922 | Maier | 128/249 |
| 2,032,101 | 2/1936 | Sullivan | 128/200.28 |
| 2,560,215 | 7/1951 | Christensen | 128/200.28 |

FOREIGN PATENT DOCUMENTS 692146 10/1930 France .................................. 128/249

Primary Examiner—John D. Yasko
Attorney, Agent, or Firm—Nilsson, Robbins, Dalgarn, Berliner, Carson & Wurst

[57] ABSTRACT

Apparatus is disclosed for quickly delivering a flow or spray of an eyewashing liquid such as water to the eyes of the wearer of a helmet or hard hat. A reservoir of appropriate liquid is formed within the helmet or hard hat. Air pressure is applied to the body of liquid by means of an associated pneumatic priming pump. Conduits communicate between the reservoir and duct members which are positioned to direct the flow of liquid into the eyes of the user. The duct members are opened by the pulling of a string which releases plugs located therein.

9 Claims, 4 Drawing Figures

EYEWASHING APPARATUS

BACKGROUND AND SUMMARY OF THE INVENTION

The present invention relates to means for washing the eyes of harmful substances. In particular, it is directed to a helmet or hard hat including such means.

Various head mounted devices have been disclosed in the prior art wherein a supply or flow of water is directed to the head or face of the wearer. Each design reflects the peculiar needs of a given application. For instance, in the cosmetics art, U.S. Pat. No. 3,088,459 of Rabinoff titled "Therapeutic Cosmetic Mask" discloses a mask including means for supplying hot liquid in the form of needle sprays under pressure to the face of a person wearing the mask. The mask is subsequently capable of applying cold liquid to the user's face to close the pores of the skin and wash off the residue of any previously applied medication. The patent discloses a pair of tanks 14, 16 separate from the mask, for providing the liquid. Another device in this realm, U.S. Pat. No. 2,507,386 of Spiegel titled "Head Treating Apparatus", discloses a double-walled cap which encloses the hair on the user's head. A hair dye or any other hair or scalp treating liquid may be introduced between the walls of the cap through an opening in the outer wall. The liquid is caused to seep through minute orifices in the inner wall of the cap and onto the user's scalp and hair by the massaging of the cap.

In the practice of various hazardous and semi-hazardous occupations, the utility of protective equipment associated with and/or mounted upon the head is evident. Various contaminants present in the work environment may hinder the workman and endanger his health. U.S. Pat. Nos. 2,032,101 of Sullivan titled "Fume and Dust Eliminator" and 2,632,163 of Spandau titled "Protective Outfit" disclose representative devices of this nature. The protection of the eyes of the worker poses special problems. Chemicals and particles which may enter the eye must be quickly removed to avoid severe injury, up to and including blindness. Often hazardous conditions are encountered at locations remote from a hose or other water supply. This is commonly the case with regard to high rise construction. Thus there exists a need in the workplace for an eyewash apparatus which is quick-acting, portable and non-burdensome to the wearer.

These and other needs are addressed by the present invention wherein there is provided apparatus for washing the eyes. The apparatus includes a helmet. The helmet includes a region for storing a volume of eyewashing liquid. Means are provided for directing the eyewashing liquid from the region toward the eyes of the user.

In a further aspect, there is provided an eyewashing system for a helmet. The eyewashing system provides a region for storing a volume of eyewashing liquid within the helmet. Means are then provided for directing the eyewashing liquid from the region toward the eyes of the wearer of the helmet.

These and other aspects, advantages and features of the present invention will become apparent from the detailed description to follow wherein like numerals refer to like parts throughout.

DETAILED DESCRIPTION

Figure 1:
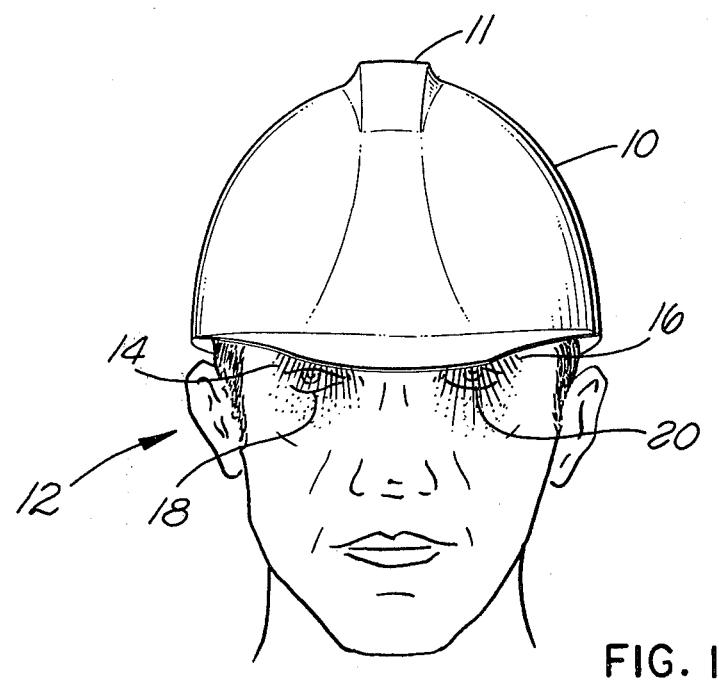
FIG. 1 is a frontal view of a hard hat in use incorporating the present invention.

FIG. 1 is a frontal view of the present invention activated to provide an eye-cleansing spray of liquid to the wearer of a hardhat. One can see that the helmet or hardhat, having an outer shell 10 with upper crown 11, is seated upon the head of the wearer 12 in a conventional manner. In accordance with the present invention, streams of water or other eyewashing liquid are directed to the right and left eyes 18, 20 of the wearer 12. The streams of water 14, 16 will be seen to be quickly activated to wash away chemicals and/or other contaminants which have entered the eyes. Such contaminants are often capable of severe damage to the eyes 18, 20, both mechanical and chemical, upon prolonged contact. Thus the quick rinsing action provided by the present invention, featuring the streams 14, 16 initiated by the pulling of a simple release string, is essential for the workman's safety.

Figure 2:
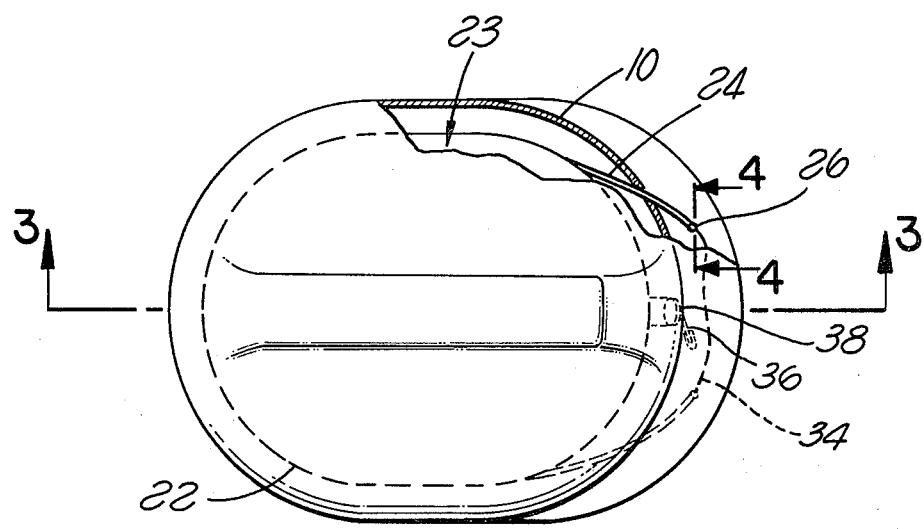
FIG. 2 is a top view of the helmet of the present invention.

FIG. 2 is a top view of the hardhat. A dashed line 22 indicates the outline of a reservoir 23 of water or eyewashing liquid formed at the top of the outer shell 10 of the helmet. The liquid is loaded into the reservoir, confined between the center shell 10 and a liner, by providing a plug or other conventional sealable orifice apparatus in the outer shell 10 or in the liner (discussed below). A conduit 24 is shown which serves to transfer the liquid from the reservoir 23 toward the front of the helmet. A similar conduit is located symmetrically with respect to the center line 3—3 of the helmet. Each conduit terminates in a duct, such as the duct 26, through which the eyewashing liquid may emerge. The attitude of the ducts is adjusted through conventional levelling and adjusting screws or like means which allow precise aiming of the spray at the eyes of the wearer. A chinstrap may be provided to stabilize the hardhat upon the wearer's head to assure that the ducts remain properly aimed.

Figure 4:
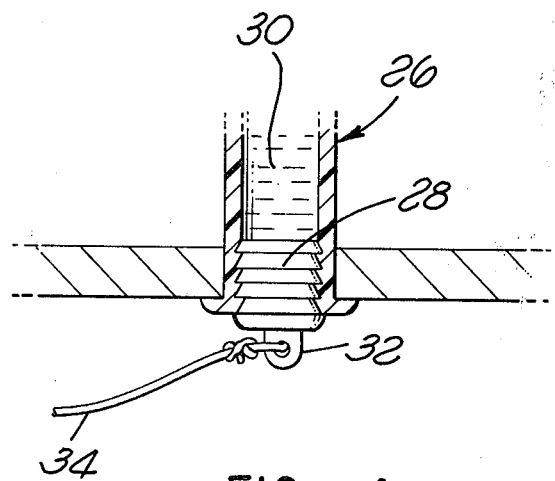
FIG. 4 is an enlarged side sectional view of the duct apparatus taken along the line 4—4 of FIG. 2.

FIG. 4 is an enlarged cross-sectional view of the duct 26, with which conduit 24 terminates, taken along the line 4—4 of FIG. 2. As can be seen in this figure, a plug 28 (not shown in FIG. 2) is inserted into the duct 26 to prevent the flow of liquid 30 therethrough. An eyelet 32 provides the point of attachment for a release string 34. The other end of the release string 34 is engaged to the eyelet of an identical plug fitted to the duct terminating the other, symmetrically oriented, conduit. Plug 28 is so dimensioned with respect to the duct 26 as to be released therefrom by a tug of the string 34. The requisite force for removing the plug is such as to allow its removal and consequent activation of the streams of eyewashing spray without the radical alteration of the position of the hard hat. Thus the sprays from the ducts are not misdirected by the application of the release force to the eyewashing system. On the other hand, the plug 28 is retained within the duct 26 with sufficient force to resist the air pressure applied to the liquid 30, discussed below.

Returning to FIG. 2, one can see that there is provided a lock pin 36 which may be slidably fixed at one of two positions. The pin 36 secures the position of a handle 38 of a cylindrical pneumatic priming pump 40, shown in FIG. 3, which serves to pressurize the liquid in the reservoir 23.

Figure 3:
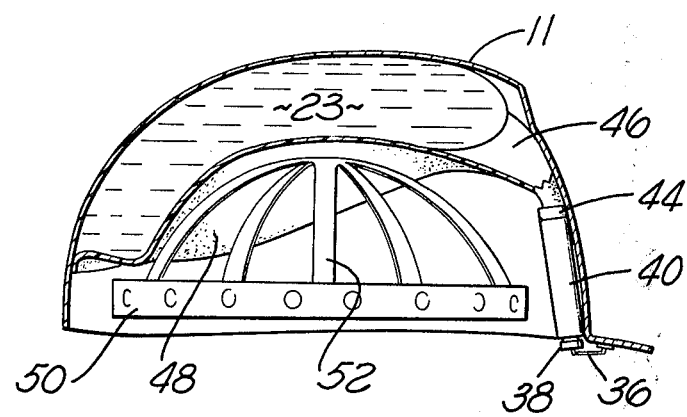
FIG. 3 is a side sectional view of the helmet of the present invention taken along the line 3—3 of FIG. 2.

FIG. 3 is a cross-sectional view of the helmet taken along the line 3—3 of FIG. 2. One can see that a large portion of the reservoir 23 is stored beneath the crown 11 of the shell 10 of the hardhat. A flap valve 44 is interposed between the pump 40 and the reservoir 23 to prevent the liquid within the reservoir from entering the pump. An air space 46 is pressurized by means of the priming pump 40 which exerts like pressure upon the substantially incompressible fluid within the reservoir 23.

The reservoir 23, as shown in FIG. 3, is contained between the outer shell 10 of the hardhat and an inner liner 48. Both the shell 10 and the liner 48 are of plastic or other appropriate watertight composition. The addition of an inner liner 48 does not interfere with the wearing of the hardhat as such a hat is conventionally suspended from the wearer's head by means such as a headband 50 including cross members 52. The reservoir 23 may be confined in alternative arrangements located between the shell 10 and the wearer's head. For example a watertight bag of accordian-like shape might be provided between the liner 48 and the shell 10 to retain the liquid.

In operation, the wearer pressurizes the liquid contained in the reservoir 23 by pumping the handle 38 of the pump 40 a number of times. The presence of adequate pressure is indicated by significant resistance to further pumping. The wearer then locks the handle 38 in its compressed condition by moving the lock pin 36 to secure the pressure within the air space 46. He may than proceed to wear the apparatus as he would a conventional hardhat. In the event that it should become necessary to apply a stream of eyewashing liquid or water to his eyes, the user need only pull upon a string 34, removing the plugs from their ducts and releasing a flow of pressurized air and water aimed toward his eyes.

Thus it is seen that there has been brought to the art a new and improved hardhat incorporating means for providing a stream of eyewashing liquid to cleanse the eyes of the wearer. By means of the invention disclosed herein, which is highly portable and quick-acting, a workman can quickly direct a stream of eyewashing liquid to purge contaminants from the eyes.

What is claimed is:

1. Apparatus for washing the eyes comprising:
   a. a helmet;
   b. said helmet including a region for storing a volume of eyewashing liquid; and
   c. means for directing said eyewashing liquid from said region toward the eyes of a wearer.

2. Apparatus as defined in claim 1 wherein the means for directing said eyewashing liquid includes at least one conduit, said conduit being in communication with said region for storing a volume of eyewashing liquid.

3. Apparatus as defined in claim 2 wherein the means for directing said eyewashing liquid further includes means for applying pressure to said volume of eyewashing liquid.

4. Apparatus as defined in claim 3 wherein said means for directing said eyewashing liquid further includes means for activating a flow of said eyewashing liquid.

5. Apparatus as defined in claim 4 wherein said means for activating a flow includes a release string.

6. Apparatus as defined in claim 3 wherein said pressure is air pressure.

7. Apparatus as defined in claim 6 wherein said means for applying pressure is an air pump.

8. Apparatus as defined in claim 1 wherein
   a. said helmet includes a shell and a liner; and
   b. said region comprises a reservoir formed between said shell and said liner.

9. Apparatus as defined in claim 1 wherein said eyewashing liquid is water.

* * * * *